United States Patent
Holman et al.

(10) Patent No.: US 7,419,563 B2
(45) Date of Patent: Sep. 2, 2008

(54) METHODS OF MAKING MEDICAL DEVICES

(75) Inventors: Thomas J. Holman, Princeton, MN (US); Afsar Ali, Maple Grove, MN (US); Stacie Depner, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 107 days.

(21) Appl. No.: 11/166,027

(22) Filed: Jun. 23, 2005

(65) Prior Publication Data

US 2006/0289112 A1 Dec. 28, 2006

(51) Int. Cl.
B32B 37/00 (2006.01)

(52) U.S. Cl. ............... 156/272.2; 156/272.8; 156/275.1; 156/309.6

(58) Field of Classification Search ................ 156/158, 156/272.8, 275.1, 308.2, 308.4, 309.6; 285/21.2
See application file for complete search history.

(56) References Cited

U.S. PATENT DOCUMENTS

| | | | |
|---|---|---|---|
| RE32,056 E | | 12/1985 | Granzow et al. |
| 4,574,173 A | | 3/1986 | Bennett |
| 4,942,000 A | * | 7/1990 | Penoyer ...................... 264/448 |
| 5,425,903 A | | 6/1995 | Sloane, Jr. et al. |
| 5,514,236 A | * | 5/1996 | Avellanet et al. ............ 156/154 |
| 5,749,825 A | | 5/1998 | Fischell et al. |
| 6,056,844 A | | 5/2000 | Guiles et al. |
| 6,123,719 A | | 9/2000 | Masychev |
| 6,409,863 B1 | * | 6/2002 | Williams et al. ............ 156/198 |
| 6,596,217 B1 | | 7/2003 | Davis-Lemessy et al. |
| 6,740,191 B2 | | 5/2004 | Clarke et al. |
| 6,858,104 B2 | | 2/2005 | Flanagan |
| 6,913,056 B2 | | 7/2005 | Landherr et al. |
| 7,156,285 B2 | * | 1/2007 | Sergey et al. ............ 228/234.1 |
| 2002/0153149 A1 | * | 10/2002 | Okada et al. ............... 174/35 R |
| 2002/0165523 A1 | | 11/2002 | Chin et al. |
| 2003/0055483 A1 | | 3/2003 | Gumm |
| 2003/0141002 A1 | | 7/2003 | Flanagan |
| 2004/0172121 A1 | | 9/2004 | Eidenschink et al. |
| 2005/0261666 A1 | | 11/2005 | Larson |

OTHER PUBLICATIONS

Parker, Sybil, "McGraw-Hill Dictionary of Scientific and Technical Terms," 1984, McGraw-Hill Book Company, Third Edition.*
"ANTEC 2002 Plastics : Annual Technical Conference, vol. 1: Processing," 2002, Society of Plastics Engineers.*

* cited by examiner

*Primary Examiner*—Jeff H Aftergut
(74) *Attorney, Agent, or Firm*—Fish & Richardson P.C.

(57) ABSTRACT

Methods of making medical devices are disclosed. In some embodiments, a method for welding together two components is described. The two components are non-coaxial and contact one another. A fixture holds the two components in a desired configuration. Electromagnetic radiation is directed at an area where the two components are in contact. The radiation causes the two portions to fuse together. The fixture has an open area or a transmissive material in the path of the electromagnetic radiation so that at least a portion of the radiation impinged up on the two components.

21 Claims, 6 Drawing Sheets

METHODS OF MAKING MEDICAL DEVICES

TECHNICAL FIELD

The invention relates to methods of making medical devices, such as catheters.

BACKGROUND

A balloon catheter is one type of medical device that can be introduced into the body to treat various conditions. For example, the balloon catheter can be used to treat conditions of the heart (such as in balloon coronary angioplasty or stent delivery) or to treat non-vascular conditions (such as obstructions of the gall bladder or bile duct).

A balloon catheter typically includes an elongated shaft and an inflatable balloon carried by the shaft. The shaft includes a lumen in fluid communication with the interior of the balloon. During use, the balloon is initially in a deflated condition so that it can be delivered through a narrow, tortuous path to a target site. At the target site, the balloon can be inflated by introducing a fluid, such as a liquid, through the lumen of the shaft and into the balloon. Subsequently, the balloon catheter can be removed by removing the fluid, thereby deflating the balloon, and withdrawing the catheter.

Various techniques can be used to make a balloon catheter. For example, to bond the balloon to the shaft, adhesive bonding and thermal bonding (such as ultrasonic welding and laser bonding) can be used.

SUMMARY

The invention relates to making medical devices, such as catheters. The devices are formed by joining together one or more components with radiation.

In one aspect, the invention features methods of making a medical device having a first component and a second component. The first component and the second component are held with a fixture, the first and second components being non-coaxial and in contact at a contact area. The fixture comprises a first section and a second section configured to hold the first and second components. The first and second components are joined together in at least a portion of the contact area.

The method can include one or more of the following features. Electromagnetic radiation, such as ultraviolet light, infrared light, or visible light, can be directed at the contact area to join the two components together. The radiation can pass through a portion of the fixture. The fixture can include a non-polymeric material, such as silica, germanium, and zinc selenide, or a polymeric material, such as polyethylene, polycarbonate, polyacrylate, polymethylpentene, polyester, polyetheretherketone (PEEK), polyphenylene oxide (PPO), polyamides, polytetrafluoroethylene, or fluorinated EPC. The radiation can be directed through a mask before impinging upon the contact area. The radiation can be directed to the contact area from a plurality of angles. Different (or multiple) wavelengths of electromagnetic radiation can be used to join the components together. An output radiation can be sensed. The electromagnetic radiation can be controlled and stopped when a predetermined quantity of output radiation is sensed. The fixture can be cooled. A member, such as a mandrel, can extend through one of the components to support the component. The mandrel can be heated by RF. The mandrel can be cooled. The sections of the fixture can contact one another. The fixture can have portions that contact one another when the components are held together. The components can be formed from a polymeric material or metal. Heat can be delivered to the contact area of the components, such as by radiofrequency, for example, contacting metal particles to the contact area that are capable of heating by radiofrequency. At least one of the components can be supported by a metallic member and the metallic member can be heated. The components can be tangential to one another.

In another aspect, the invention features a fixture. The fixture is capable of holding a first component and a second component non-coaxially and in contact with one another. The fixture has first and second sections configured to hold the first and second components.

Embodiments of aspects of the invention may include one or more of the following features. The fixture can be formed of a material that has a transmission percentage of greater than 10% relative to a selected electromagnetic radiation. The fixture can be formed from an optical material. The material can be transmissive to one or more of ultraviolet light, infrared light and visible light. The fixture can be formed from a non-polymeric or a polymeric material. The fixture can include one of silica, germanium, a metal oxide and zinc selenide. The fixture can include a beam mask. The fixture can include one or more recesses. The recesses can have curved surfaces. The fixture can be made of either a rigid material, a flexible material, or a combination thereof. The fixture can include metal, such as in an area adjacent to where the two components contact one another. The fixture can include apertures configured for cooling or heating fluid. The fixture can have multiple members configured to fit together. The fixture can be configured to apply pressure to the two components nested within the fixture. The fixture can hold the components tangent to one another.

In another aspect, the invention features a method of making a medical device having a first component and a second component. The method includes holding the first component and the second component with a fixture, the first and second components being non-coaxial and in contact at a contact area. The fixture comprises a non-polymeric material. The first and second components are joined together in at least a portion of the contact area. The non-polymeric material can be, for example, an inorganic solid state material or non-heat shrink material.

Embodiments may have one or more of the following advantages. A fixture can hold the two components together in a desired orientation to one another. The fixture may control the location of a weld between the components. The fixture may enable reproducible welds over a series of devices. The fixture can apply pressure to the desired portion of the components so that the portions of the components weld together when electromagnetic radiation is applied.

The number of components that are not damaged by the fusing or welding process can be increased by use of the methods described herein. The fixture can allow for cooling, so that each weld may be performed under controlled conditions, that is, the fixture can be kept from heating up from a weld process. Cooling the fixture may keep the components from becoming overheated outside of the area where the weld is to be formed. Restricting the heating of the elements to the portions that are not to be welded together may avoid undesired distortion of the components. Welding the components with a mandrel inside the components may prevent the components from deforming during welding.

Sensing the emission from the components during welding may indicate when the weld is complete, thereby allowing for closed-loop control of the welding system. The components can be kept from being exposed to excess radiation with the closed loop control, thereby potentially further avoiding damage to the components. Radiation can be applied simultaneously to multiple portions of the components. Applying radiation from multiple sides of the weld can prevent uneven fusing. Also, the application of heat can be more accurately and precisely directed than from one side alone. A beam mask can further define the area to which radiation is applied. The beam mask may prevent unnecessary application of radiation to portions of the components that are not to be fused together.

Forming the fixture from optical materials, such as fused silica or BK7, can allow for high percentages of transmission of incident electromagnetic radiation with little or no diffraction. Germanium and zinc selenide can also enable high transmission efficiency and beam manipulation. If the beam is efficiently transmitted to the desired location, the weld may be formed quickly.

The fixture described above can hold the two components together in a desired orientation to one another. The fixture can control the location of a weld between the components. The fixture allows for reproducible welds over a series of devices. The fixture applies pressure to the desired portion of the components so that the portions of the components weld together when electromagnetic radiation is applied.

In the fixture embodiments where no optical material is used, the range of materials from which the fixture can be formed is large.

In some embodiments, there is no need to use a heat shrink material to weld two components together, which can reduce the thickness to the device since no additional layer is required. Desired characteristics, such as flexibility and dimension, can be easier to obtain without additional layers of material. Eliminating the heat shrink material can also reduce cost of manufacturing because the fixtures described herein can be reused.

With a laser, such as a carbon dioxide laser, a weld can be formed between two non-opaque polymer materials. Thus, the components of the medical device do not need to be formed from an opaque material as with some methods. A greater range of materials can be selected from when making the device when an opaque material is not required.

Other aspects, features and advantages will be apparent from the description of the embodiments thereof and from the claims.

DETAILED DESCRIPTION

Figure 1A:
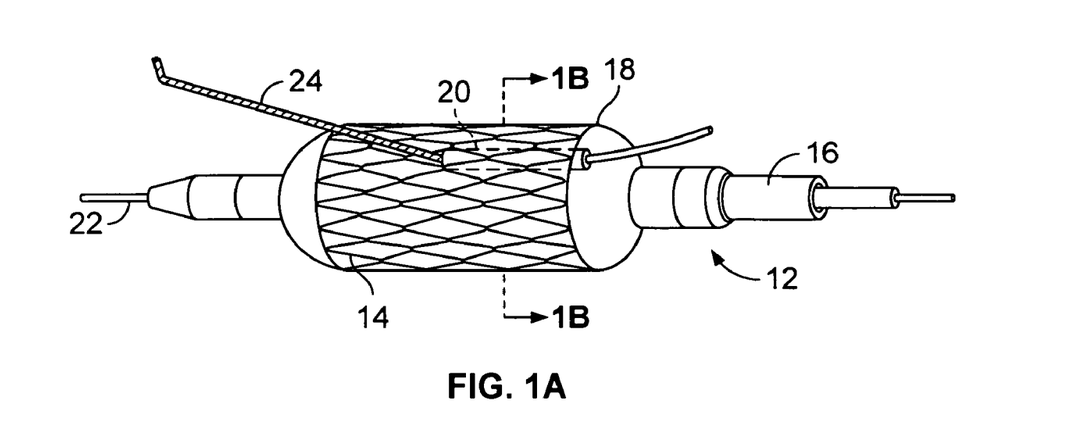
FIG. 1A is a perspective view of an embodiment of a stent delivery system.
Figure 1B:
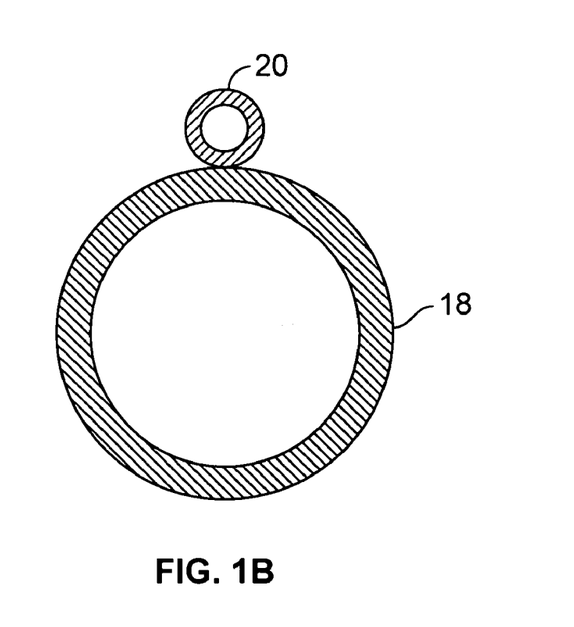
FIG. 1B is partial, cross-sectional view of the stent delivery system of FIG. 1A, taken along line 1B-1B.

Referring to FIGS. 1A and 1B, a stent delivery system 10 includes a balloon catheter 12 and a stent 14 carried by the balloon catheter. Balloon catheter 12 includes a polymeric catheter shaft 16, a polymeric inflatable balloon 18 rotatably carried by the catheter shaft, and a polymeric sidebranch tube 20 non-coaxially attached to the balloon (FIG. 1B). Catheter shaft 16 is configured to receive a first guidewire 22, and sidebranch tube 20 is configured to received a second guidewire 24. Stent delivery system 10 can be used to deliver stent 14 to a variety of locations within the body, but the system is particularly well-suited for delivering the stent to an adjacent branch of a vessel bifurcation. Examples of stent delivery systems, including methods of using the systems, are described in Gumm, U.S. Patent Application Publication 2003/0055483; Eidenschink et al., U.S. Patent Application Publication 2004/0172121; and Fischell et al., U.S. Pat. No. 5,749,825.

Figure 2:
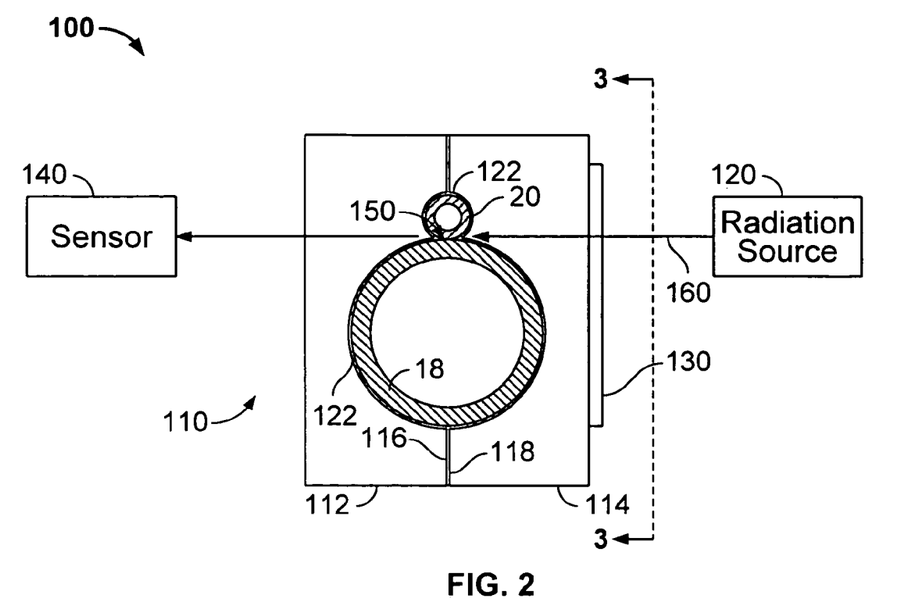
FIG. 2 is a cross-sectional view of an embodiment of a system for joining components.
Figure 3:
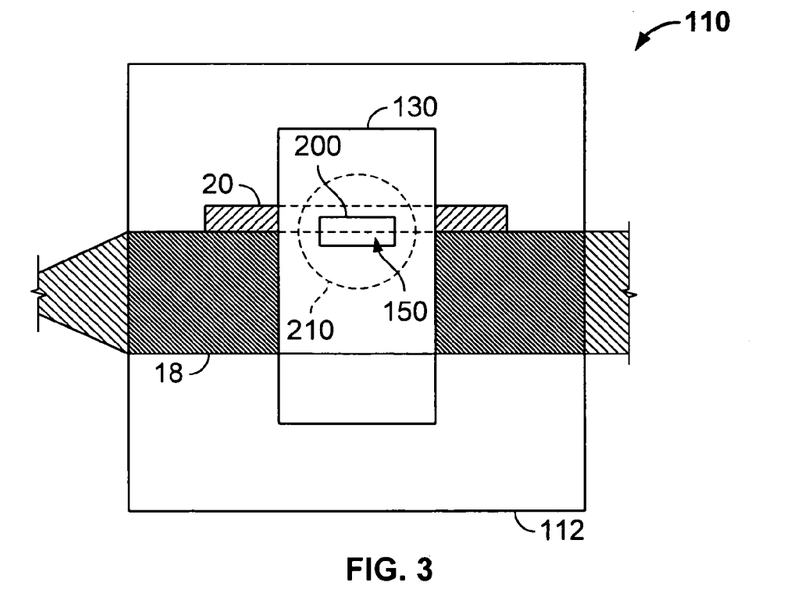
FIG. 3 is a diagrammatic, side view of the system of FIG. 2, taken along line 3-3.

Referring to FIGS. 2 and 3, a system 100 for bonding two components, such as a balloon 18 and tube 20, of a medical device is shown. System 100 includes a fixture 110 that is configured to hold balloon 18 and tube 20 in a desired orientation, an electromagnetic radiation source 120, a beam mask 130, and a sensor 140. As shown, fixture 110 is configured to hold balloon 18 and tube 20 in a non-coaxial (e.g., tangential) relationship such that the balloon and the tube contact one another in a contact area 150. Radiation source 120, such as a laser, is configured to direct an energy beam 160 through beam mask 130 and to contact area 150. Sensor 140, such as an infrared radiation sensor, is configured to detect heat emitted from contact area 150. During use, fixture 110 holds balloon 18 and tube 20 in contact under a desired pressure. Radiation source 120 then passes energy beam 160 through beam mask 130 to selectively direct energy to contact area 150, thereby bonding balloon 18 and tube 20 together in at least a portion of the contact area. Sensor 140 detects the amount of heat emitted from contact area 150, and at a predetermined heat level, the energy applied from radiation source 120 is stopped. Subsequently, additional components can be bonded using the same system 100.

Fixture 110 generally includes two or more sections that cooperate to secure two or more components in a desired arrangement or orientation for bonding. As shown in FIGS. 2 and 3, fixture 110 includes a first section 112 and a second section 114 that have mating surfaces 116, 118 that contact one another when the sections cooperate to secure the selected components to be bonded. When sections 112, 114 come together to retain the selected components, the sections are configured to define one or more (as shown, two) recesses 122 that are sized to receive the selected components, and to hold the components in contact at a preselected orientation and under a preselected pressure at contact area 150.

Fixture 110 includes (e.g., has at least a portion that is formed of) a transmissive material that is capable of allowing a percentage of the electromagnetic radiation from radiation source 120 to pass to contact area 150. For example, section 114 can be wholly formed of one or more transmissive materials; or the section can have a portion (e.g., a window) through which beam 160 passes that is formed of a transmissive material, and the remaining portions of the section can be formed of a non-transmissive or less transmissive material. The transmissive material can substantially transmit beam 160, so that there is little to no transmission loss, or the transmissive material may only transmit a percentage of the beam energy, such as at least about 25% to about 95% of the beam. The thickness of the transmissive material can determine the amount of radiation that can be transmitted through the material, so in some implementations, the portion of fixture 110 through which beam 160 passes has a thickness that is less than the thickness of other portions of the fixture to enhance transmission of beam 160. Expressed another way, the transmissive material may have a transmission coefficient of at least about 10% (for example, at least about 20%, at least about 40%, at least about 60%, or at least about 80%) relative to a selected incident wavelength.

The transmissive material can be any material with the transmission characteristics described above. The material can be one that does not bond to the components when the components are fused together. However, a small amount of the transmissive material or other materials used to form fixture 110 can fuse to the components with little to no negative effect. The material is also selected to have characteristics such that the body does not deform or alter its shape when the components are fused, for example, the transmissive material is a non-shrinking member. The transmissive material or other materials used to form fixture 110 can be harder than the material from which the components are made. In some embodiments, the transmissive material can be made of a rigid material or a flexible material. The transmissive material and/or other materials used to form fixture 110 can be non-polymeric or polymeric. Examples of non-polymers include inorganic, solid state materials such as glasses, minerals, optical materials, and other materials having an infinite lattice structure. Specific examples of materials include fused silica or BK7, germanium, zinc selenide, alkali halides (such as NaCl, KCl, KBr, CsBr, and CsI), metal fluorides (such as LiF, $MgF_2$, $CaF_2$, $SrF_2$, and $BaF_2$), metal halides (such as AgCl, AgBr, TlBrCl, and TlBrI), metal oxides (such as MgO, $Al_2O_3$ (e.g., sapphire), $SiO_2$, and $ZrO_2$), chalcogenides (such as ZnS, CdS, CdSe, and CdTe), groups IV and III-V materials (such as C, Si, and GaAs), or glasses (such as borosilicates, fluorozirconates and arsenic trisulfide). Examples of polymers include polyethylene, polycarbonate, polyacrylate, polymethylpentene, polyester, polyetheretherketone (PEEK), polyphenylene oxide (PPO), polyamides, polytetrafluoroethylene, or fluorinated EPC. The polymer should be able to withstand the heat generated during bonding, for example, by having a melting point greater than about 160° C., for example, from about 160° C. to about 450° C. The transmissive material can be selected based on the electromagnetic radiation that is to be applied to the components to be joined. For example, for infrared radiation, germanium or zinc selenide can be selected as the transmissive material, and for visible wavelength radiation, a fused silica optical material can be selected. Different sections of fixture 110 can be formed from different materials, according to the radiation source and/or sensor in system 100.

Radiation source 120 can be any device capable of delivering electromagnetic radiation to contact area 150. Examples of radiation sources include any laser, such as a diode that can deliver radiation in the infrared, visible, or ultraviolet wavelengths, a $CO_2$ laser or an excimer laser. Radiation source 120 is positioned in system 100 so that beam 160 emitted from the radiation source impinges upon contact area 150 or a portion thereof. The alignment of radiation source 120 with fixture 110, and more specifically, with contact area 150, can be based on the refractive index of the transmissive material through which beam 160 is passed, which can help the beam contact the desired portion of the components to be joined.

Sensor 140 can be any device capable of detecting radiation or heat emitted from contact area 150. For example, sensor 140 can be an infrared sensor or sensors described in U.S. Pat. No. 6,858,104. The portion of fixture 110 between the components to be joined and sensor 140 can include a material that is transmissive to infrared radiation, such as zinc selenide. Sensor 140 is positioned in system 100 so that radiation emitted from contact area is detected by the sensor, which allows for closed loop control of the bonding process, as described further below.

Beam mask 130 is a device that stops some of energy beam 160 and allows some of the energy beam to pass and to impinge onto contact area 150. Beam mask 130 can be formed of a material, such as a metal foil, that is non-transmissive to beam 160. Referring to FIG. 3, beam mask 130 includes an opening or a hole 200 of any desired shape, such as a circle, an oval, a rectangle or a rounded rectangle, that allows beam 160 to pass through the opening. During use, the initial cross-sectional area of energy beam 160 is reduced to the area of opening 200, and the reduced area of the beam is substantially aligned with contact area 150 or a portion thereof. Beam mask 130 can be positioned outside of fixture 110, embedded within the fixture, and/or formed on a wall of one or more recesses 122. Beam mask 130 can be a surface coating on fixture 110. In some implementations, a non-transmissive or low transmission coating is formed on the fixture, which blocks a portions of the beam 160 from passing through the fixture.

Figure 4:
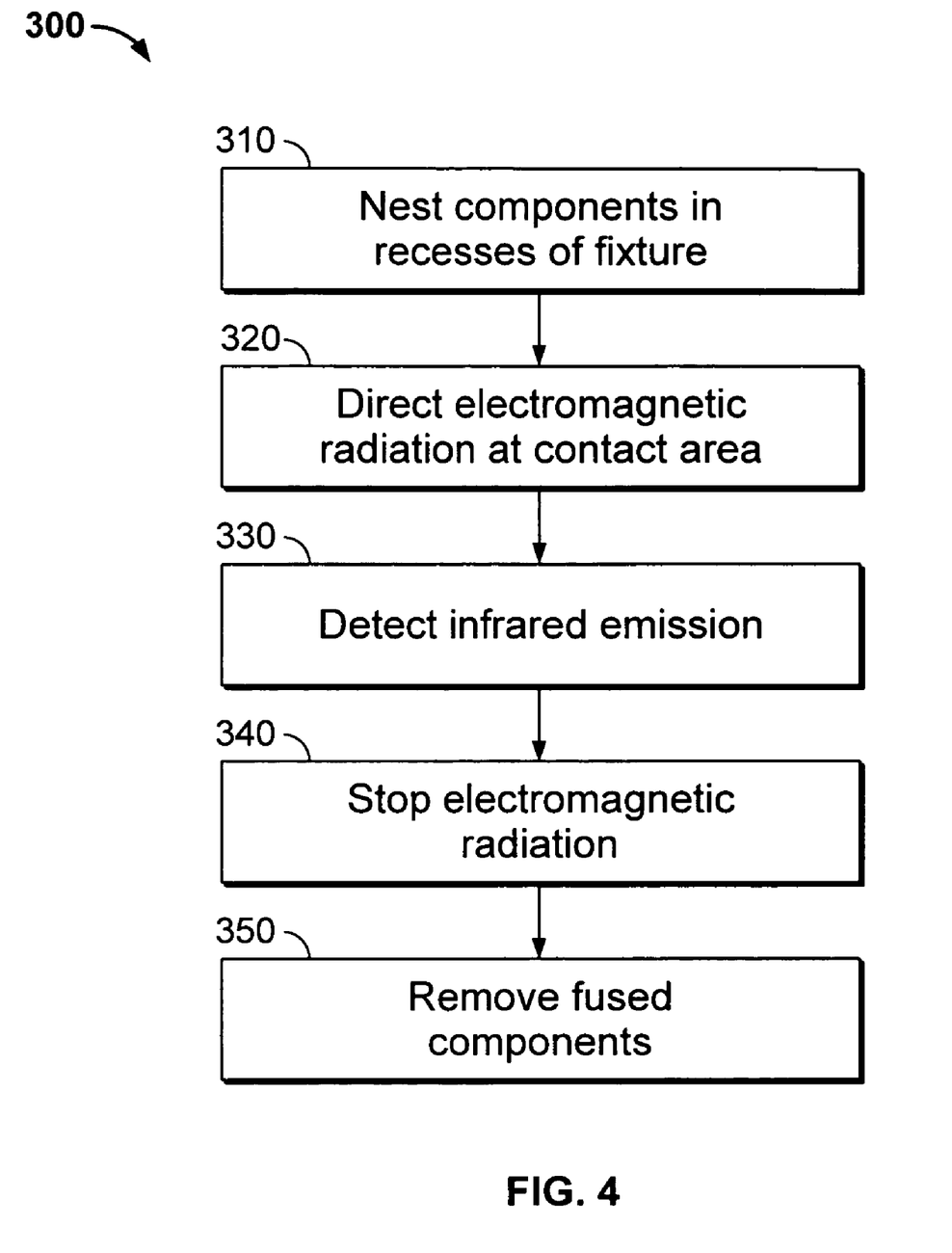
FIG. 4 is a flow chart for an embodiment of a method of joining components.

Referring to FIG. 4, a process 300 of joining two components together using system 100 is shown. First, the components, such as balloon 18 and tube 20, are nested into their respective recesses in fixture 110, and the sections of fixture are brought together (step 310). One or more fasteners, such as a screws or clamps, can be used to hold the components in place and/or to hold sections of fixture 110 together so that the two components are squeezed together at contact area 150.

Radiation source 120 is then activated and energy beam 160 is directed at contact area 150 (step 320). Beam 160 travels from radiation source 120, passes through beam mask 130, passes through a portion of fixture 110, and impinges on contact area 150. Beam 160 can be directed at the components from any desirable angle, and beam mask 130 can be used to allow only selected portions of the components' surfaces to be impinged with radiation. The radiation that strikes the components causes the components to fuse together in at least a portion of contact area 150.

As energy beam 160 is directed to contact area 150, sensor 140 detects the heat or radiation emissions from contact area 150 (step 330). When a predetermined threshold emission is detected, a signal is communicated to radiation source 120 to stop emitting radiation (step 340). Closed loop control of laser welding is further described in Flanagan, U.S. Pat. No. 6,858,104.

The joined components can then be removed from fixture 110 and allowed to cool (step 350). Additional components can then be fused together using the same fixture 110 and method, or another component can be fused to one or both of the joined two components, as desired.

While a number of embodiments have been described, the invention is not so limited.

Figure 5:
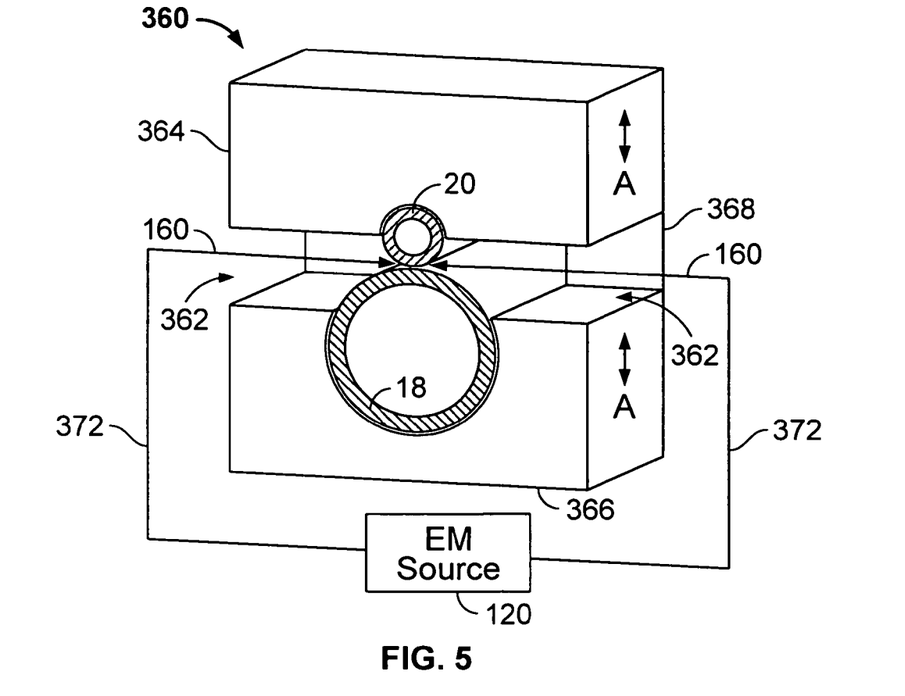
FIG. 5 is a diagrammatic, perspective view of an embodiment of a system for joining components.
Figure 6:
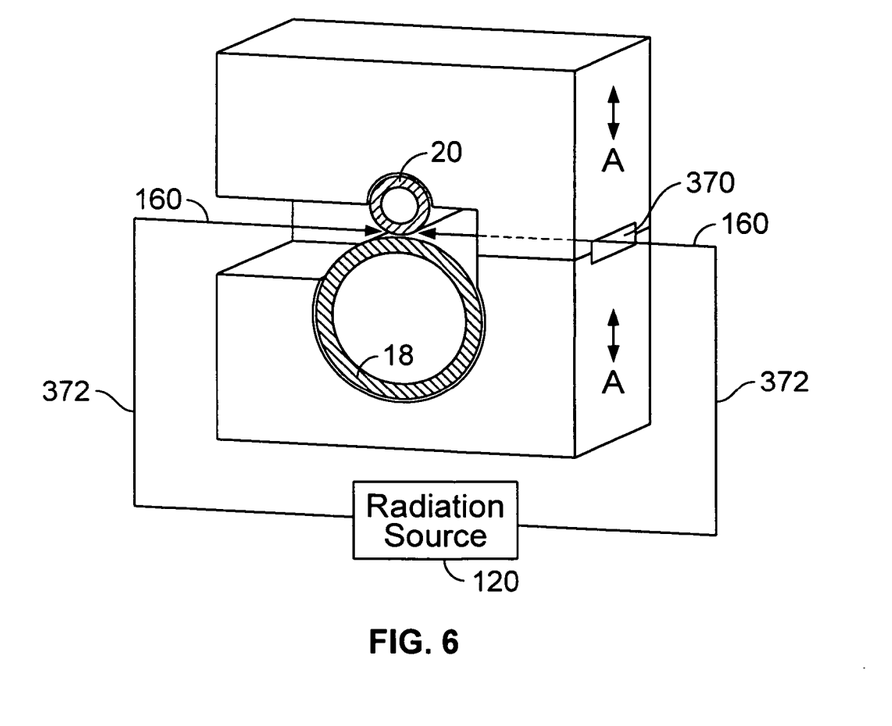
FIG. 6 is a diagrammatic, perspective view of an embodiment of a system for joining components.

As an example, energy beam 160 from radiation source 120 need not pass through a portion of a fixture. Referring to FIG. 5, a fixture 360 can be formed to include one or more openings 362 that are free from any material and allow energy beam 160 to pass directly through to the components to be joined. As shown, fixture 360 includes two sections 364, 366 that are movable (arrows A) to engage their respective components (as shown, balloon 18 or tube 20), and to hold the components together. As shown, sections 364, 366 do not directly contact one another and a securing mechanism 368, such as fastener, including a band or a clip, holds the sections together. In other embodiments, referring to FIG. 6, fixture 360 includes sections that contact one another when their respective component are held together, and the sections define an opening 370 free of material through which energy beam 160 can pass. Opening 370 can also act as a beam mask. In some embodiments, fixture 360 is a monolithic and unitary structure defining recesses into which the components are compressed and inserted. Fixture 360 can be formed from a material that is transmissive and/or non-transmissive to energy beam 160.

As another example, multiple energy beams 160 can be delivered to contact area 150 during the joining process. Referring again to FIG. 5, radiation source 120 can be in communication with a fiber optic delivery system, such as a bifurcated fiber optic delivery system, that allows multiple fiber optic lines 372 to extend from radiation source 120. Lines 372 enable a beam from a single radiation source to apply radiation to the components from multiple sides and/or angles. Alternatively or additionally, multiple radiation sources 120 can be used. Fusing the components together from multiple sides and/or angles prevents one portion (e.g., side) from not receiving a greater amount of radiation than another portion, and provides uniform fusing.

Figure 7:
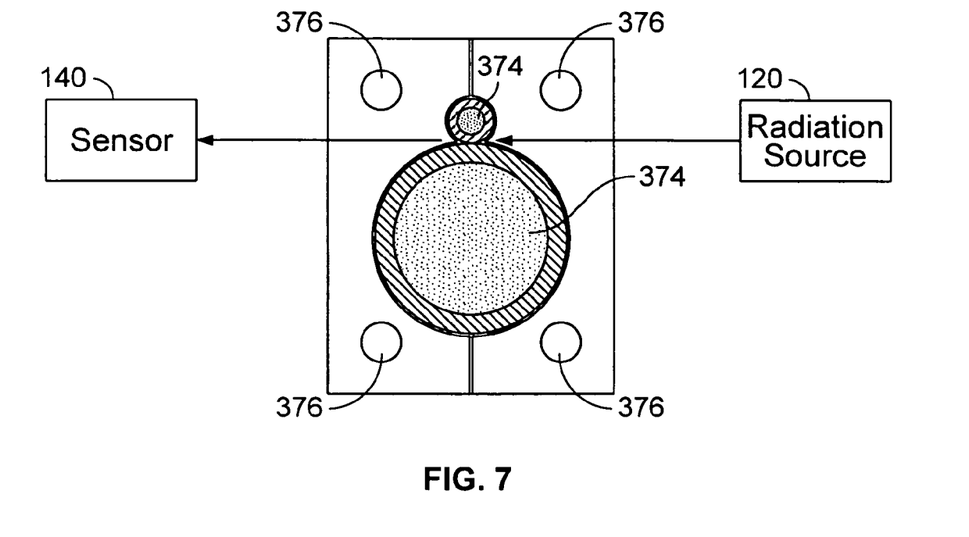
FIG. 7 is a cross-sectional view of an embodiment of a system for joining components.

Referring to FIG. 7, in some embodiments, in addition to supporting the components to be joined with a fixture, one or more mandrels 374 can be inserted into one or more components to support the component(s). Mandrel(s) 374 can secure the placement of the component(s) and keep the component(s) from becoming misshapen before or during fusing. Mandrel(s) can be formed from metal or other suitable material to avoid fusing the mandrel(s) to the component(s).

Still referring to FIG. 7, one or more sections of a fixture described herein can include one or more channels 376 for cooling fluid. Channels 376 can extend run parallel to the components and allow the fluid, such as a coolant, to flow through the channels to maintain a desired temperature for the fixture. Flowing a coolant through channels 376 can reduce overheating of the fixture during the joining process, which can reduce undesirable heat transfer to the components to be joined.

Additionally or alternatively, one or more hollow mandrels can be used to cool the components by flowing a coolant through the mandrel(s). The hollow mandrel(s) can be inserted into the component(s) to support the component(s) as well as to cool the component(s). In some embodiments, a coolant can be flowed through a lumen of a component, without using a mandrel.

Figure 8:
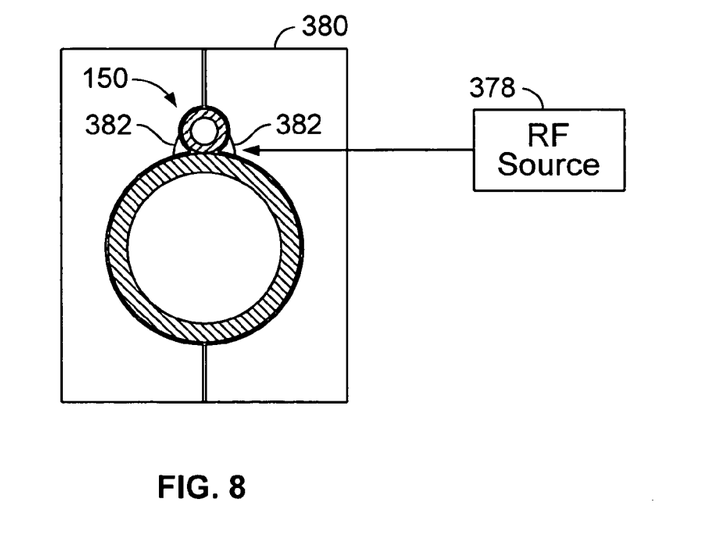
FIG. 8 is a cross-sectional view of an embodiment of a system for joining components.

Other forms of electromagnetic radiation can be applied to contact area 150 to join the components. For example, the components can be joined together using radiofrequency (RF) heating or magnetic effects. Referring to FIG. 8, a polymer compounded to include a material (such as magnetic particles) that is susceptible to heating by magnetic effects (such as hysteresis effects) can be placed in contact area 150. Upon exposure to a magnetic field, as shown, from RF source 378, the compounded polymer is heated to join the components. Magnetic particles are available as the Smartbond™ System (Triton Systems, Inc., Chelmsford, Mass.), and heating by magnetic effects is discussed in U.S. Pat. No. 6,056,844.

Alternatively or additionally, resistive heating can be used to join the components. Still referring to FIG. 8, a fixture 380 includes one or more conducting portions 382 that can include a conducting material, such as a metal. The remaining portions of fixture 380 is formed of a material that is substantially resistant to deforming or melting when the components are bonded together. Conducting portions 382 are configured to contact the components, for example, proximate to contact area 150. During the joining process, a current can be passed through conducting portions 382 to resistively heat the conducting portions and portions of the components contacting the conducting portions, thereby joining the components. Conductive portions 382 can extend to the outer surface of fixture 380 or can be enclosed by a non-conducting material.

Examples of polymers from which the components can be formed include thermoplastics and thermosets. Examples of thermoplastics include, for example, polyolefins, polyamides, such as nylon 12, nylon 11, nylon 6/12, nylon 6, and nylon 66, polyesters, polyethers, polyurethanes, polyureas, polyvinyls, polyacrylics, fluoropolymers, copolymers and block copolymers thereof, such as block copolymers of polyether and polyamide, e.g., Pebax®; and mixtures thereof. Examples of thermosets include elastomers such as EPDM, epichlorohydrin, nitrile butadiene elastomers, silicones, etc. Conventional thermosets such as epoxies, isocyanates, etc., can also be used. Biocompatible thermosets, for example, biodegradable polycaprolactone, poly(dimethylsiloxane) containing polyurethanes and ureas, and polysiloxanes, may also be used. Other materials are described in commonly assigned U.S. Ser. No. 09/798,749, filed Mar. 2, 2001, and entitled "Multilayer Medical Device". One or more of these materials can be used in a component, in any combination. The polymers to be join may be miscible or non-miscible. Welding of non-miscible polymers, for example, by using a compatibilizer, is described in Davis-Lemessy, U.S. Pat. No. 6,596,217.

While the joining processes described above refer to joining of polymeric components, the processes are not so limited. For example, the joining processes can be used to join a polymeric component (such as a catheter shaft) to a non-polymeric component (such as a metal hypotube or a metal reinforcing wire) by melting at least a portion of the polymeric component in the contact area.

Figure 9A:
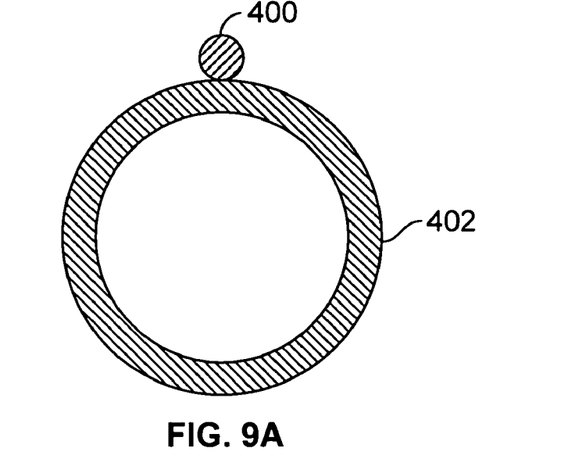
FIGS. 9A, 9B, and 9C show embodiments of two joined components.
Figure 9B:
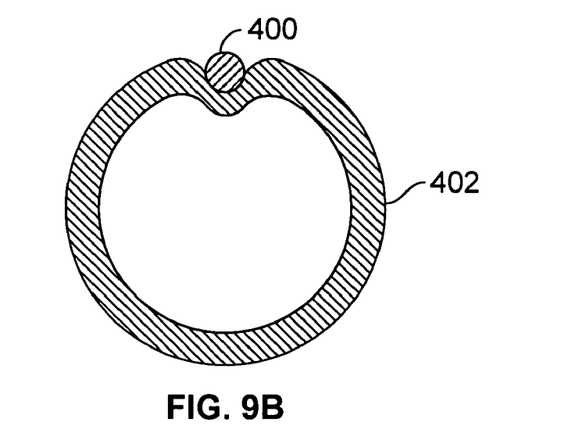
Figure 9C:
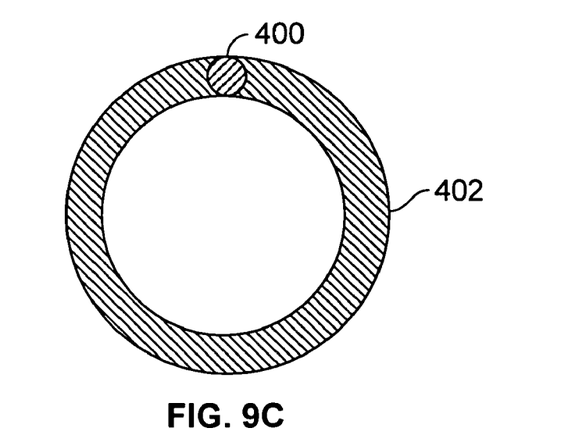

The systems and processes described herein can be used to join two components to varying degrees. FIG. 9A shows a first component 400 (such as a metal reinforcement wire) joined non-coaxially to an outer surface of a second component 402 (such as a catheter shaft). FIG. 9B shows first component partially embedded in second component 402. FIG. 9C shows first component 400 fully embedded or encapsulated within second component 402. The degree of joining or embedding can be controlled by the amount of time that energy is focused on contact area and the pressure applied by the fixture.

In addition to the fixtures described above, the recesses of a fixture can be oriented so that the first component is other than non-coaxially or tangentially aligned with the second component. The fixture can hold the two components in any desired configuration, such as at a diagonal to one another, wrapped around one another, or co-axially to one another.

In some embodiments, a first radiation source is directed to one part of contact area 150 while one or more different radiation sources are directed to other part(s) of the contact area. The radiation sources can have different characteristics based on the materials of the components and the desired weld characteristics.

More than two components of a medical device can be welded to form the device at one time. For example, a fixture may include three sections that together define three recesses to hold three components. The three components can be welded together at one time. For example, a wire can be integrated into a wall of a lumen and a second lumen and be welded to the wall or three or more lumens can be welded together.

All references, such as patents and patent application publications, indicated herein are incorporated by reference in their entirety.

Other embodiments are within the claims.

What is claimed is:

1. A method of making a medical device having a first component and a second component, the method comprising:

holding the first component and the second component with a fixture, the first and second components being non-coaxial and in mutual contact at a contact area, the fixture comprising a first section and a second section configured to hold the first and second components, the first section having a first mating surface and the second section having a second mating surface that contacts the first mating surface when the sections cooperate to hold the components together; and while holding the first component and second component in mutual contact within the fixture, directing electromagnetic radiation at the contact area to join the first and second components together in at least a portion of the contact area and flowing a coolant through the fixture to maintain the fixture at a temperature while joining the first and second components.

2. The method of claim 1, wherein the electromagnetic radiation is selected from the group consisting of ultraviolet light, infrared light, and visible light.

3. The method of claim 1, wherein the electromagnetic radiation passes through a portion of the fixture.

4. The method of claim 3, wherein the fixture comprises a non-polymeric material.

5. The method of claim 4, wherein the non-polymeric material is selected from the group consisting of silica, germanium, a metal oxide, and zinc selenide.

6. The method of claim 3, wherein the fixture comprises a polymeric material.

7. The method of claim 6, wherein the polymeric material is selected from the group consisting of a polyethylene, polycarbonate, polyacrylate, polymethylpentene, polyester, polyetheretherketone (PEEK), polyphenylene oxide (PPO), polyamides, polytetrafluoroethylene, and fluorinated EPC.

8. The method of claim 1, further comprising directing the electromagnetic radiation through a mask before the radiation is directed to the contact area.

9. The method of claim 1, wherein directing the electromagnetic radiation comprises directing electromagnetic radiation to the contact area from a plurality of angles.

10. The method of claim 1, further comprising sensing an output radiation.

11. The method of claim 10, further comprising controlling the electromagnetic radiation directed to the contact area in response to the output radiation.

12. The method of claim 11, further comprising stopping the electromagnetic radiation directed to the contact area when a predetermined quantity of output radiation is sensed.

13. The method of claim 1, further comprising supporting at least one of the components with a member extending through the at least one of the components.

14. The method of claim 1, wherein the fixture comprises a material that is more rigid than at least one of the components.

15. The method of claim 1, wherein at least one of the components comprises a polymeric material.

16. The method of claim 1, wherein at least one of the components comprises a metal.

17. The method of claim 1, wherein the fixture includes a fastener and holding the first cylindrical component and the second cylindrical component includes fastening the fastener to hold the first section and the second section together.

18. The method of claim 1, wherein the first component is a tube and the second component is a balloon.

19. The method of claim 1, wherein holding the first component and the second component does not including holding with a heat shrink material.

20. The method of claim 1, wherein when the first section and the second section are brought together, the fixture has one or more recesses sized to receive the first component and the second component.

21. The method of claim 1, wherein the electromagnetic radiation is directed along a path tangential to the first component and the second component.

* * * * *